United States Patent
Christodoulou

(10) Patent No.: US 7,075,647 B2
(45) Date of Patent: Jul. 11, 2006

(54) BACK-SCATTER DETECTION IN FLOW CYTOMETERS

(75) Inventor: Christodoulos Christodoulou, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 10/881,856

(22) Filed: Jun. 30, 2004

(65) Prior Publication Data

US 2006/0001875 A1    Jan. 5, 2006

(51) Int. Cl.
*G01N 21/00* (2006.01)

(52) U.S. Cl. ..................................... 356/339

(58) Field of Classification Search ........ 356/335–343; 250/574, 575, 227.28; 385/114–116
See application file for complete search history.

(56) References Cited

U.S. PATENT DOCUMENTS

| 5,125,737 | A | 6/1992 | Rodriguez et al. |
| 6,177,277 | B1 * | 1/2001 | Soini ............ 436/63 |
| 6,228,652 | B1 | 5/2001 | Rodriguez et al. |
| 2004/0036874 | A1 * | 2/2004 | Kramer ............ 356/342 |
| 2004/0036875 | A1 | 2/2004 | Kramer |

* cited by examiner

*Primary Examiner*—Tu T. Nguyen
(74) *Attorney, Agent, or Firm*—Warren W. Kurz; Mitchell E. Alter

(57) ABSTRACT

A method and apparatus for detecting back-scattered light from small particles, such as blood cells, irradiated by a focused beam of light as such particles travel through the interrogation zone of a standard optical flow cell in a flow cytometer. Back-scattered light is collected at a location upstream of the beam-shaping optics (or a portion of such optics), at a location between the light beam source and the beam-shaping optics.

9 Claims, 4 Drawing Sheets

BACK-SCATTER DETECTION IN FLOW CYTOMETERS

BACKGROUND OF THE INVENTION

1. Field of the Invention

This invention relates to the field of flow cytometry and, more particularly, to improvements in apparatus and methods for detecting back-scatter (i.e., radiation scattered or reflected backwardly) from irradiated particles passing through an optical flow cell of a flow cytometer.

2. The Prior Art

The use of light-scattering (LS) measurements as a means for differentiating various types of small particles, e.g., blood cells, in a liquid suspension is well known. For example, in virtually all sophisticated flow hematology instruments and fluorescence flow cytometers, it is common to measure the forward light scattering properties of individual blood cells by passing the cells, one at a time, through the "interrogation zone," i.e., the constricted region, of an optically transparent flow cell. While positioned within such interrogation zone, each blood cell is irradiated by a focused laser beam, and one or more photodetectors, strategically positioned forward of the interrogation zone, operate to sense the level of forward-scattered radiation, usually within different predetermined angular ranges. In addition to detecting a portion of the forward-scatter signature of the irradiated cells, some cytometric instruments measure side-scatter as well, using a separate photodetector located laterally of the irradiated cells to radiation scattered at approximately 90 degrees to the irradiating beam. These light-scattering measurements are often combined with other simultaneously made measurements, e.g., axial light-loss, DC volume and/or RF conductivity measurements, to better differentiate particles and cells of particular interest from other cells and particulate material in the sample having similar forward and side-scattering properties within the measurement ranges. See, for example, the disclosure of the commonly assigned U.S. Pat. Nos. 5,125,737, and 6,228,652, both being issued in the names of Rodriguez et al. Having made various different parametric measurements on each cell, the cytometric instrument produces scattergrams in which the different parameters measured are plotted against each other. Ideally, each cell or particle type appears on these scattergrams as a tight cluster of data points, each point representing an individual cell or particle in the sample, and each cluster being readily identifiable from other clusters by a clearly identified spacing that separates various clusters in the scattergram. In such case, it is a relatively simple matter to "gate" cells of one cluster from those of another cluster and to enumerate the cells of each cluster. This ideal, unfortunately, is sometimes difficult to realize since, for a variety of reasons, a certain percentage of cells of one type invariably invade the spatial domain of cells of other types, making the differentiation of each type somewhat imprecise.

To more precisely differentiate certain blood cells and the like on the basis of their light-scattering signature, it has been suggested to further determine a portion of the back-scatter signature (i.e., the intensity-distribution of radiation (light) reflected back towards the irradiating source) of such cells. In the commonly assigned U.S. application Ser. No. 10/227,004 filed in the name of D. Kramer on Aug. 23, 2002, a back-scatter collector/detector is disclosed that is adapted for use in a conventional flow cytometer to collect and detect a portion of the back-scattered light from an irradiated cell as it passes through an optical flow cell. The light-collecting component of such a device comprises a plurality of optical fibers, each having a light-collecting end supported by a housing that serves to arrange such ends in a circular array. A central bore hole in the fiber-supporting housing enables the cell-irradiating laser beam to pass uninterrupted through the housing (and the center of the fiber array) as the beam propagates from its source towards the cell interrogation zone of the flow cell. The light-discharge end (opposite the light-collecting end) of each optical fiber is optically coupled to a high-gain photo-detector, e.g., a photomultiplier tube, which provides a signal indicative of the level of light collected by the fiber ends. It may be appreciated that the angle at which the back-scatter light is detected from each cell is determined by both the diameter of the circular array of fiber ends, and the displacement between the scatter source, which is nominally the center of the cell interrogation zone, and the fiber ends. As the diameter of the array increases and/or the displacement between the flow cell center and the fiber ends decreases, the back-scatter angle of detection increases, and vice versa.

In light-scatter measurement systems of the above type, the cell-irradiating laser beam is typically brought to focus within the cell-interrogation zone by a beam-shaping lens system located on the beam axis between the light beam source and the flow cell. Such a lens system usually comprises a pair of spaced plano-convex lenses having perpendicularly-crossed optical powers. By this arrangement, one lens serves to focus the laser beam in a first plane while the other serves to focus the laser in a second plane perpendicular to the first plane, whereby a desired elliptical focus pattern is achieved. The two lenses are commonly supported in a desired spaced relationship, typically about 50 to 70 mm. apart, within the barrel of a cylindrical housing. The size of the focus spot is determined by the respective focal lengths of the lenses. Different spot sizes afford different advantages. For example, larger spots may be useful in differentiating relatively large cells, and smaller spots may be required to achieve a relatively high flux density, as may be necessary to excite certain fluorochromes to which certain cells of interest have been previously coupled for detection. To achieve a small spot size, the focal length of the front lens (i.e., the lens closer to the flow cell) must be relatively short which, unfortunately, reduces the space between the front lens and the front wall of the flow cell wall. Typically, the front lens of the optical system has a focal length of about 10 to 15 mm., and the rear lens (i.e., the lens further from the flow cell) has a focal length of about 60 to 80 mm.

In the above-noted Kramer application, the optical fibers of the back-scatter collector are arranged in a relatively tiny circular array having a diameter of only about 1.75 mm. Each optical fiber in the array has a nominal diameter of 500 microns, and there are about 20 fibers in the array. As described, the back-scatter collector is to be positioned within the above-noted space between the front lens of the laser-focusing system and the front wall of the optical flow cell. While the disclosed back-scatter collector can be readily positioned within this space when the focal length of the front lens is 15 mm. or greater, proper placement of the collector becomes considerably more difficult (if not impossible) as the focal length of the front lens of the focus system approaches 10 mm. It will be appreciated that the distance between the center of the flow cell's interrogation zone and the outside wall of the flow cell consumes a portion of the focal length distance. Thus, though the focal length of the rear lens may be 10 mm., the actual space in which the back-scatter collector may be positioned will be somewhat shorter. Further, even were it possible to position the circular array of fiber ends of a back-scatter collector of the type described above within an axial space as short as 10 mm., the angle at which back-scatter would be detected by the circular array of fibers can become excessively large (due the close spacing between the array and the center of the cell-interrogation zone of the flow cell).

SUMMARY OF THE INVENTION

In view of the foregoing discussion, an object of this invention is to provide a back-scatter-detection method in which the position of the light-collecting optics of the back-scatter detector is independent of the focal length of the front lens of the afore-noted beam-shaping optics.

According to the invention, the light-collecting optics of a back-scatter detector are positioned upstream (i.e., in the direction of the laser beam source) of the front lens of the beam-shaping optics, either between the front and rear lenses of the beam-shaping optics, or even upstream of the rear-most lens of such optics. As a result of this arrangement, the focal length of the front lens of the beam-shaping optics presents no limitation on the size, placement and optical alignment of the back-scatter collecting optics, and such optics may be positioned, with comparative ease, in the relatively large space between the two lenses of the beam-shaping optics, or in the significantly larger space between the laser source and the rear lens of the beam-shaping optics. Further, as a result of this arrangement of elements, back-scattered light at much smaller back-scatter angles can be detected, thereby giving rise to a higher signal-to-noise ratio of the back-scatter signal.

According to a first aspect of the invention, improved apparatus is provided for detecting the intensity of back-scatter from individual particles passing seriatim through an interrogation zone of an optical flow cell. As each particle passes through such interrogation zone, it is irradiated by a light beam propagating along an optical axis perpendicular to the direction of travel of the particles through the interrogation zone. The apparatus of the invention comprises light-focusing means positioned on the optical axis for focusing the light beam in the interrogation zone; and a back-scatter collector for collecting back-scattered light from irradiated particles traveling through the interrogation zone. Most significantly, and in contrast to the prior art teachings, the back-scatter collector is positioned on the optical axis upstream of at least a portion of the light-focusing means, between the light source and such portion of the light-focusing means. According to the more preferred embodiment, the light focusing means comprises a pair of spaced lenses, and the back-scatter collector is positioned between such lenses. According to another preferred embodiment, the light focusing means comprises a pair of spaced lenses, and the back-scatter collector is positioned upstream of both of such lenses.

According to a second aspect of the invention, an improved method is provided for detecting back-scatter from cells or other small particles irradiated by a focused light beam while traveling through an optical flow cell of a flow cytometer. As suggested above and in accordance with the present invention, the back-scattered light from the cells is collected at a location upstream of the beam-shaping optics used to focus the light beam on the cells.

The invention and its advantages will be better understood from the ensuing detailed description of preferred embodiments, reference being made to the accompanying drawings in which like reference characters denote like parts.

DETAILED DESCRIPTION OF PREFERRED EMBODIMENTS

Figure 1:
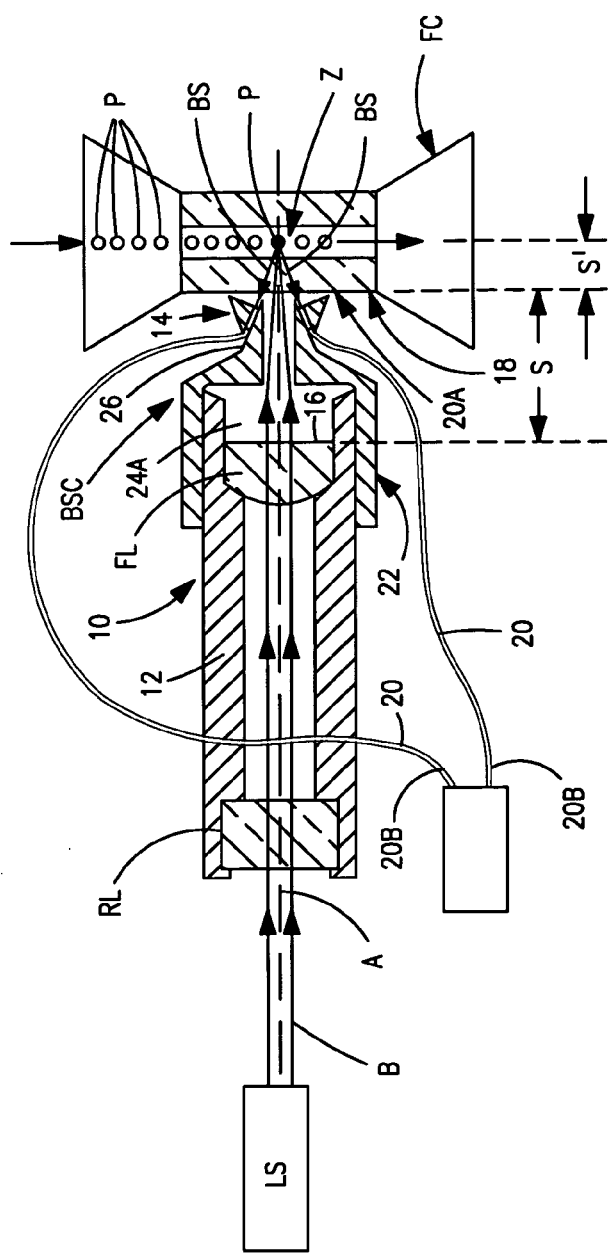
FIG. 1 is a schematic side illustration of a prior art system for detecting back-scatter from particles irradiated by a light beam in an optical flow cell of a conventional flow cytometer.

Referring now to the drawings, FIG. 1 schematically illustrates a conventional approach for collecting and detecting back-scattered light BS scattered by small particles P, such as blood cells, upon being irradiated by a focused "light" beam B while passing through the constricted interrogation zone Z of a transparent optical flow cell FC of the type commonly found in conventional flow cytometers. (Note, the word "light" is used herein in a broad sense to refer to electromagnetic radiation in general, not necessarily that found in the visible region of the electromagnetic spectrum. Typically, however, the radiation used in flow cytometers to irradiate particles and cells is found within the near-ultraviolet to the near-infrared region of the spectrum.) The stream of particles passing through the flow cell is maintained at or near the center of zone Z by a hydrodynamic focus flow scheme in which the stream is confined by a sheath liquid flowing through the flow cell simultaneously with the particle stream. The irradiating light beam B is commonly provided by a laser source LS, e.g., a helium-neon or argon laser, and such light beam is brought to focus at the center of zone Z by a beam-shaping lens system 10 located on the beam axis A. Lens system 10 commonly comprises a pair of spaced cylindrical lenses FL and RL that operate together to focus the beam to a desired elliptical shape (e.g., 10 by 80 microns in size) at the center of the particle-interrogation zone Z. The beam-shaping lenses are commonly supported in a desired spaced relationship by a cylindrical lens barrel 12.

As noted above, the conventional approach for collecting and detecting the back-scattered light from irradiated particles is to position the light-collecting optics 1.4 of the back-scatter collector BSC in the relatively small space S separating the front surface 16 of the forward lens FL of the beam-shaping optics (i.e., the lens surface closest to the flow cell FC), from the front face 18 of the optical flow cell. As described in the above-noted application of Kramer (Ser. No. 10/227,004), the back-scatter collector BSC may comprise a plurality of optical fibers 20, each having a light-collecting end 20A through which light can enter the fiber for transmission by multiple internal reflections, and a light-discharge end 20B through which the transmitted light emerges. The respective light-collecting ends of the optical fibers are supported in a circular array by a housing 22, better shown in FIG. 2. In use, the circular array of fibers is located at a position such that back-scattered light from an irradiated particle or cell enters the light-collecting end of each fiber. Back-scattered light transmitted by each fiber is detected at the fiber's discharge end by a high-gain detector, e.g. a photo-multiplier tube PMT.

Figure 2:
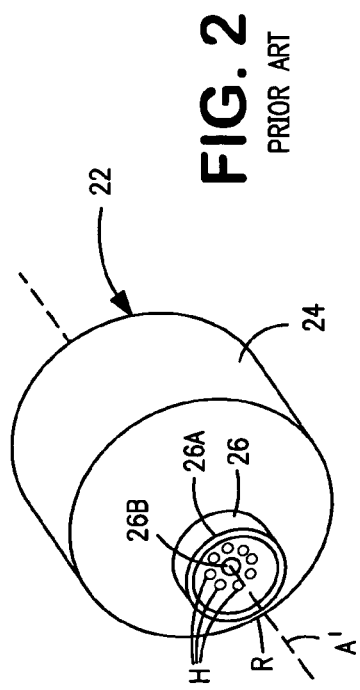
FIG. 2 is an enlarged perspective illustration of a portion of the FIG. 1 apparatus.

Referring to FIG. 2, the fiber-holding housing 22 comprises a relatively large barrel portion 24 adapted to slidingly engage, and thereby be supported by the outside surface of the cylindrical lens barrel 12 used to support the lenses of the beam-shaping optics. Barrel portion 24 tapers down to a smaller cylindrical portion 26 having a circular, fiber-holding flange 26A at its open end, and a central bore hole 26B that communicates with a much larger central bore 24A in barrel portion 24. According to the preferred embodiment of Kramer, the smaller cylindrical portion 26 has a length of about 2.5 mm., and an outside diameter of about 1.5 mm. The diameter of bore hole 26B is about 1.3 mm, just large enough to pass the particle-irradiating beam B as the beam converges towards its focal point. The enlarged barrel portion 24 has a length of about 4.0 mm., an outside diameter of about 3.3 mm.

As best shown in FIG. 2, the circular flange 26A of housing 22 is provided with a plurality of evenly spaced bore holes H, each having a diameter slightly exceeding 500 microns, the nominal diameter of each optical fiber 20. The bore holes H are arranged in a circular pattern to form a ring R centered about the central longitudinal axis A' of the housing. In use, axis A' is coincident with beam axis A. Preferably, ring R has a diameter of about 1.75 mm. which determines, together with the spacing between the fiber ends and the back-scatter source, the angle at which back-scatter is detectable. The diameter of ring R cannot be significantly reduced owing to manufacturing considerations and the need to transmit the irradiating beam through the ring's center. The front end of the flange 24A is spherically concave, and the axis of each fiber hole H is normal to the concave surface, whereby the respective fiber axes converge at the anticipated location of the scatter source which, in use of the device, corresponds to the center of the flow cell's interrogation zone Z. As a result of this arrangement, the scattered light is efficiently coupled into the fiber ends and transmitted through the fibers with minimal losses. This efficiency is especially important as the space between the front lens FL of the beam-shaping optics and the flow cell wall becomes shorter, as is the case when the focal length of lens FL is reduced to less than 15 mm. to achieve a relatively small spot with correspondingly high optical flux density. Ideally, the back-scatter intensity should be measured at angles less than about 25 degrees, and more preferably less than about 15 degrees. While a back-scatter collection angle of about 15 degrees may be attained in the event the focal length of lens FL is about 15 mm., it is virtually impossible to approach this angle when the focal length of lens FL is only 10 mm., a focal length that is often necessary to achieve an optical flux density sufficient to excite certain fluorochromes used to identify cells of interest. In such a case, the angle at which back-scatter can be detected cannot be reduced to less than about 25 degrees.

Now in accordance with the present invention, it has been found that back-scattered light from irradiated cells or particles passing through an optical flow cell can be collected for detection at a location upstream of the lens system (or a portion of such lens system) commonly used to focus the irradiating light beam on the cells or particles. By collecting back-scattered light at this location, the axial spacing between the beam-shaping lens and the flow cell is immaterial to the placement of the back-scatter collection optics. Moreover, by detecting back-scatter upstream of the beam-focusing lens system, the angle at which back-scatter is collectable can be reduced to only a few degrees, thereby increasing the amount of light available for detection. This has the effect of substantially improving the signal-to-noise ratio of the back-scatter signal, notwithstanding the optical absorption losses incurred by adding a lens to the optical path of the back-scattered light. Note, there is a limit to the extent to which the back-scatter angle can be reduced, that being determined by the diameter of the irradiating beam which must still be transmitted through the center of the back-scatter collection optics.

Figure 3A:
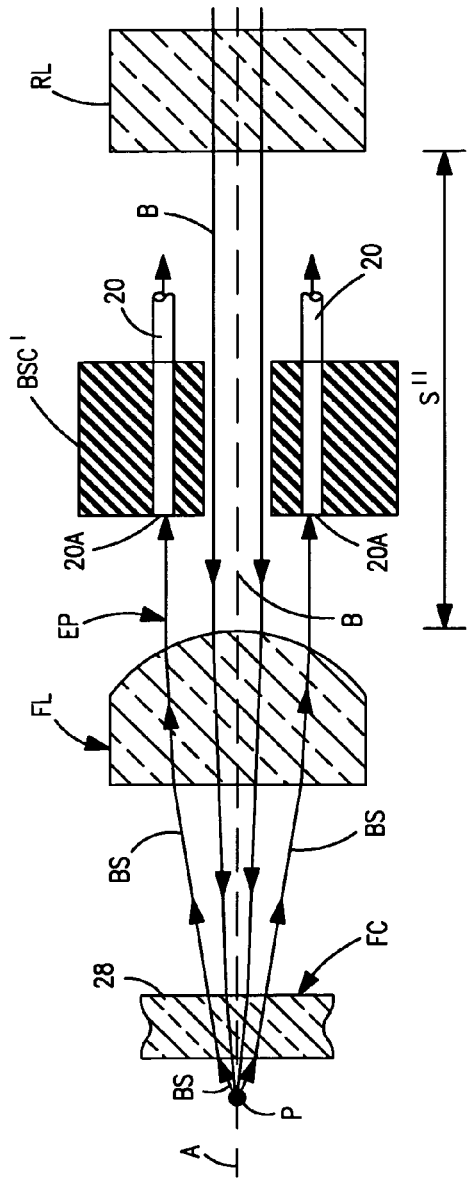
FIGS. 3A and 3B are schematic top and side views respectively illustrating apparatus for collecting back-scatter from irradiated particles in accordance with a preferred embodiment of the invention.
Figure 3B:
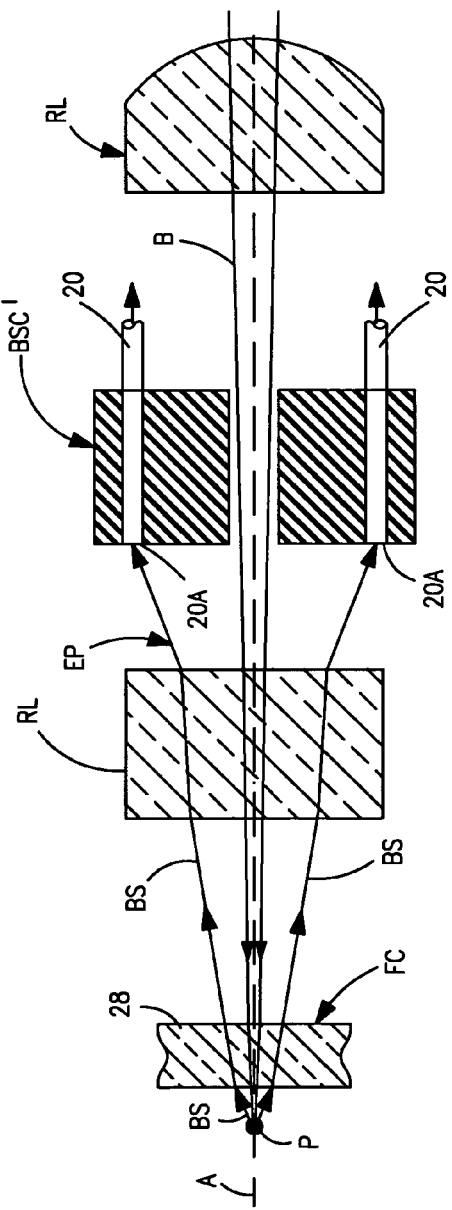
Figure 4:
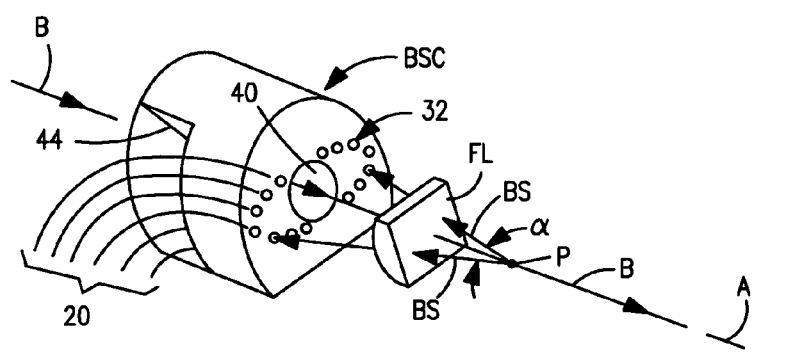
FIG. 4 is a perspective illustration of a portion of the apparatus illustrated in FIGS. 3A and 3B.

Referring to the optical diagrams of FIGS. 3A and 3B, light beam B passes through the crossed cylindrical lenses RL and FL and is thereby brought to focus on a particle P behind the front wall 28 of the optical flow cell FC. Back-scattered light BS from the irradiated particle passes back through the flow cell wall and through the forward cylindrical lens FL of the beam-shaping optics. Lens FL operates to refract the conically-expanding back-scatted light from the irradiated particle to form an expanding elliptical pattern EP. (Note, although the back-scatter light is illustrated by a pair of rays BS which define a specific angle therebetween, it will be appreciated that such light is back-scattered, in accordance with classical scattering theory, throughout a 180 degree angle. The greatest intensity of the back-scattered light will be at zero degrees (i.e., directly toward the incoming beam along axis A), and scatter intensity will vary as the scatter angle increases, depending on the characteristics of the scattering particle. However, with the exception of spikes and nulls, the overall scatter intensity will gradually decline with increasing scatter angle, and to attain the strongest back-scatter signal, the back-scatter light should be collected at or near the lowest scatter angles possible.) In accordance with a preferred embodiment of the invention, a back-scatter collector BSC', similar to that described above with reference to FIGS. 1 and 2, serves to position the light-collecting ends of a plurality of optical fibers 20 in an elliptical array 32 (or a portion of such an array, as shown in FIG. 4) to collect a portion of the back-scattered light. The dimension of the array will depend upon (a) the distance between the scatter source P and the fiber ends 20A, (b) the focal length of the lens FL, and (c) the desired nominal scatter angle α (shown in FIG. 4) of detection. The angular range will be determined by the diameter of the optical fibers.

Figure 5A:
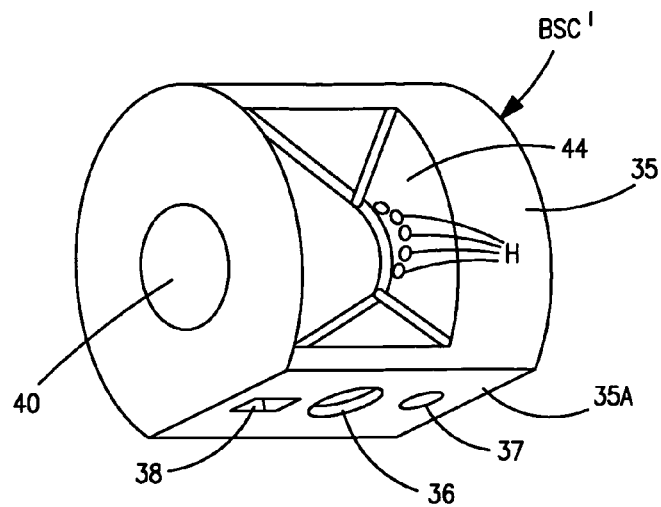
FIGS. 5A and 5B are perspective and end views, respectively, of the light-collecting portion of the apparatus illustrated in FIG. 4.
Figure 5B:
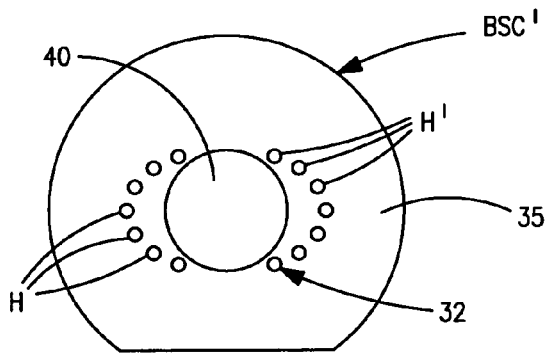

Referring to FIGS. 4, 5A and 5B, a preferred back-scatter collector BSC is shown as comprising a housing 35 that serves to support a plurality of optical fibers 20 such that their respective light-collecting ends are arranged in the above-noted elliptical array 32. Housing 35 has a planar bottom surface 35A that is adapted to engage and be supported by a planar optical support plate (not shown). A threaded hole 36 formed in surface 35 A is engaged by a threaded member (not shown) to rigidly affix the housing to the support plate. A pair of additional opening 37 and 38 cooperates with a pair of pins on the mounting plate to align the housing relative to the optical axis A. A plurality of hole H' formed in the planar front face 35B of housing 35 receive and position the light-collecting ends of fibers 20 so that the fiber ends form the desired elliptical pattern and are flush with the front face 35B. A longitudinally-extending bore hole 40 is of a diameter adapted to transmit the irradiating beam B. A pair of tapered recesses 44 formed on opposite sides of the housing facilitate the mounting of the optical fibers in the holes H.

Figure 6:
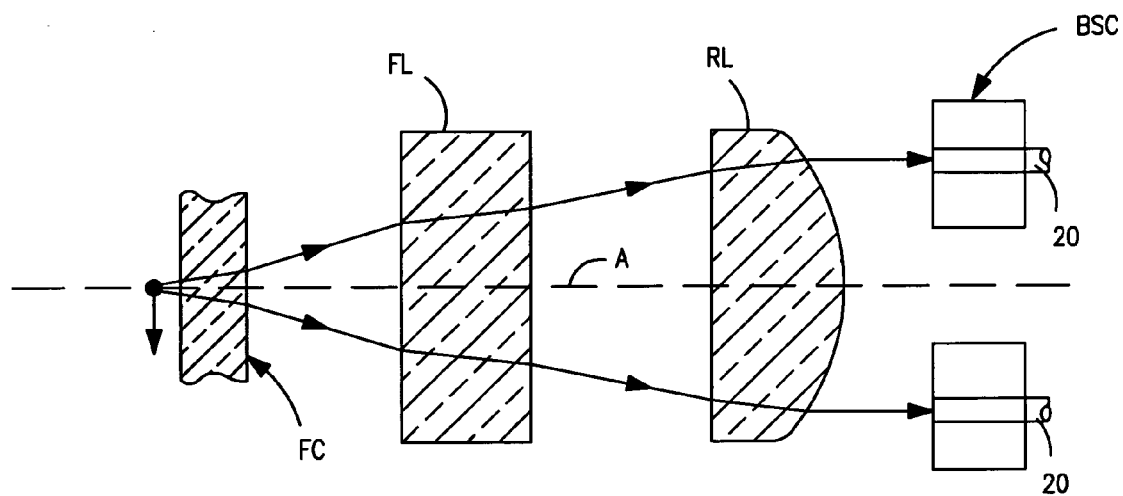
FIG. 6 is a schematic side illustration of another embodiment of the apparatus of the invention.
Figure 7:
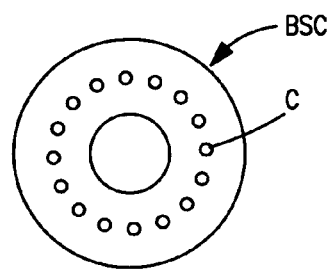
FIG. 7 is an end view of the light-collecting portion of the apparatus shown in FIG. 6.

In the embodiment disclosed above, it will be appreciated that the back-scatter collector may be positioned anywhere in the relatively large spacing S" between the front and the rear lenses of the beam-shaping optics. Preferably, however, it is desirable to place the light-collecting fiber ends relatively close to the rear surface of front lens FL since the elliptical scatter pattern being detected continues to expand in size as it passes through the front lens. Thus, the further away front the front lens, the larger the elliptical pattern of fiber ends must be to collect the light scattered at a desired scatter angle. As shown in FIG. 6, the back-scatter collector BSC" can even be arranged behind the rear lens RL of the beam-shaping optics. In this case, a circular array C of fibers (as shown in the front view of the back-scatter collector shown in FIG. 7) can be used to collect the back-scattered light since the rear cylindrical lens will convert the elliptical pattern to a circular pattern. While a circular array is advantageous from a manufacturing standpoint, the substantial increase in distance between the fiber ends and the scattering source may necessitate a larger diameter rear lens to collect the back-scattered light. Further, the scatter intensity will be reduced by an additional light-absorbing element, i.e., lens RL. Nevertheless, the same advantages of the invention are derived from this geometry, including the ability to use an extremely short focal length front lens to focus beam light on the particles as they pass through the flow cell.

While the invention has been described in detail with reference to two different preferred embodiments, it will be appreciate that various changes can be made without departing from the spirit of the invention. Such changes are intended to fall within the scope of the following claims.

What is claimed is:

1. Apparatus for detecting back-scatter from individual particles traveling seriatim through an interrogation zone of an optical flow cell, each of said particles being irradiated by a light beam emitted by a source spaced from said interrogation zone as it travels through said zone, said fight beam propagating along an optical axis perpendicular to the direction of travel of said particles and intersecting said interrogation zone, said apparatus comprising:
   light-focusing means positioned on said optical axis for focusing said light beam at said interrogation zone; and
   light-collecting means for collecting back-scattered light from irradiated particles traveling through said interrogation zone, said light-collecting means being positioned upstream of at least a portion of said light-focusing means, between said source and said portion of said light-focusing means.

2. The apparatus as defined by claim 1 wherein said light focusing means comprises a pair of spaced lenses, and wherein said light-collecting means is positioned between said lenses.

3. The apparatus as defined by claim 2 wherein said lenses are cylindrical lenses having an optical power in one plane only, and wherein said light-collecting means comprises a plurality of optical fibers each having a light-collecting end, said light-collecting ends being arranged in an elliptical array through which said light beam passes.

4. The apparatus as defined by claim 1 wherein said light focusing means comprises a pair of spaced lenses, and wherein said light-collecting means is positioned upstream of both of said lenses.

5. The apparatus as defined by claim 1 wherein said light-collecting means comprises a plurality of optical fibers each having a light-collecting end, said light-collecting ends being arranged in an endless array through which said light beam passes.

6. The apparatus as defined by claim 5 wherein said endless array is circular in shape.

7. A method for detecting back-scatter from individual particles traveling seriatim through an interrogation zone of an optical flow cell, each of said particles being irradiated by a light beam emitted by a source spaced from said interrogation zone as it travels through said zone, said light beam propagating along an optical axis perpendicular to the direction of travel of said particles and intersecting said interrogation zone, said method comprising the steps of:
   positioning a light-focusing device on said optical axis to focus said light beam at said interrogation zone; and
   collecting back-scattered light from irradiated particles traveling through said interrogation zone with a light-collecting device positioned upstream of at least a portion of said light-focusing device, at a location between said source and said portion of said light-focusing device.

8. The method as defined by claim 7 wherein said light focusing device comprises a pair of spaced lenses, and wherein said back-scattered light is collected between said lenses.

9. The method as defined by claim 7 wherein said light focusing device comprises a pair of spaced lenses, and wherein said back-scattered is collected at a location upstream of both of said lenses.

* * * * *